(12) United States Patent
Van Den Berg et al.

(10) Patent No.: US 9,334,504 B2
(45) Date of Patent: *May 10, 2016

(54) HIGH THROUGHPUT TRANSFECTION OF FILAMENTOUS FUNGI

(71) Applicant: DSM IP ASSETS B.V., Te Heerlen (NL)

(72) Inventors: Marco Alexander Van Den Berg, Echt (NL); Bianca Elisabeth Maria Gielesen, Echt (NL); Adriana Marina Riemens, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/192,236

(22) Filed: Feb. 27, 2014

(65) Prior Publication Data

US 2014/0178932 A1    Jun. 26, 2014

Related U.S. Application Data

(63) Continuation of application No. 12/306,314, filed as application No. PCT/EP2007/056311 on Jun. 25, 2007, now Pat. No. 8,697,364.

(30) Foreign Application Priority Data

Jun. 26, 2006    (EP) .................................... 06116095

(51) Int. Cl.
*C12N 15/80*    (2006.01)
*C12P 21/02*    (2006.01)

(52) U.S. Cl.
CPC ................ *C12N 15/80* (2013.01); *C12P 21/02* (2013.01)

(58) Field of Classification Search
None
See application file for complete search history.

(56) References Cited

U.S. PATENT DOCUMENTS

| 6,323,002 B1 | 11/2001 | Brody et al. |
|---|---|---|
| 7,452,707 B2 | 11/2008 | Goedegebuur et al. |
| 2004/0248258 A1 | 12/2004 | Maiyuran et al. |
| 2005/0266543 A1 | 12/2005 | Dunn-Coleman et al. |
| 2008/0156640 A1 | 7/2008 | Collins et al. |

FOREIGN PATENT DOCUMENTS

| EP | 0758020 A2 | 2/1997 |
|---|---|---|
| JP | 2005269920 A | 10/2005 |
| WO | 2004005522 A2 | 1/2004 |
| WO | 2005121351 A2 | 12/2005 |

OTHER PUBLICATIONS

Decision by European Patent Office to Revoke the European Patent No. EP-B-2 032 703, issued in Application No. 07 786 832.1-1406/2 032 703 dated Feb. 24, 2014.
DSM IP Assets B.V., Statement of Grounds of Appeal, submitted in Application No. 07786832.1-1406/2032703, Appeal No. T0967/14-3.3.08, Amended Claims and Auxiliary Request dated Jul. 7, 2014.
DSM IP Assets B.V. Notice of Appeal, submitted in Application No. 07786832.1-1406/2032703, dated Apr. 25, 2014.
Chartrain et al., Fungal Bioconversions: Applications to the Manufacture of Pharmaceuticals. In Handbook of Industrial Mycology; AN Z., ed.; Marcel Dekker: New York, NY, USA, 2005;22:563-595.
Suzuki et al., "High-Throughput Screening for Isolation of Enhanced Green Fluorescent Protein Expressing Transformants of Filamentous Fungus Using an Image Analyzer." J Biosci Bioeng. 2003;96(3);313-316.
Grimm et al., "Robotic High-Throughout Assay for Isolating Apoptosis-Inducing Genes," Biotechniques. 2002;32(3):670-677.
Gietz et al., "Transformation of Yeast by Lithium Acetate/Single-Stranded Carrier DNA/Polyethylene Glycol Method," Methods Enzymol. 2002;350:87-96.
Rines et al., "High-Content Screening of Functional Genomic Libraries," Methods Enzymol. 2006;414:530-565.
Fernandes, "Technological advances in high-throughput screening," Curr Opin Chem Bio. 1998;2(5):597-603.
Irie et al., "Efficient Transformation of Filamentous Fungus Pleurotus Ostreatus Using Single-Strand Carrier DNA", Appl. Microbiol. Biotechnol. (2001) vol. 55: 563-565.
Notice of Opposition to European Patent 2032703 B1, Jan. 3, 2012 (22 Pages).
The New International Webster's Comprehensive Dictionary of the English Language (Deluxe Encyclopedic Edition) Ed., Trident Press Int. 1996 Edition, p. 835.
Finklestein et al., "Chapter 6 Transformation", pp. 113-166 in Biotechnology of Filamenous Fungi: technology and products, Edited by: David B. Finkelsein and Christopher Ball, Butterworth-Heinemann, Stoneham USA 1992.
Oxford Dictionary of Biochemistry an Molecular Biology (Revised Edition), Oxford University Press 2006, p. 312.
Machtiger et al., "Biochemistry of bacterial membranes", Annu. Rev. Biochem. 1973 : vol. 42 pp. 575-599.
Anne et al., "Formation and regeneration of Penicillium chrysogenum protoplasts", Arch. Microbiol. vol. 98, pp. 159-166, 1974.
Karley et al., "Differential Ion Accumulation an Ion Fluxes in the Mesophyll and Epidermis of Barley", Plant Physiology, vol. 122, pp. 835-844, 2000.
Ballance et al., "Transformation of Aspergillus nidulans by the orotidine-5'-phopshate decarboxylase gene of Neurospora crassa", Biochemical and Biophysical Research Communications vol. 112, pp. 284-289, 1986.
Ballance et al., "Development of a high-frequency transforming vector for Aspergillus nidulans", Gene 36: pp. 321-331, 1985.

(Continued)

*Primary Examiner* — Jim Ketter
(74) *Attorney, Agent, or Firm* — MMWV IP, LLC.

(57) ABSTRACT

The present invention provides a method for the transfection of filamentous fungal cells, comprising providing a multitude of containers, filling into each container an amount of polymer needed for the transfection, filling the cells to be transfected as well as an aqueous solution of transfection reagent into each of the containers, incubating the resulting mixture, removing the transfection reagent from the incubated mixture; and selecting the cells which have been transformed, characterized in that the total volume of the incubating mixture is less than 1 ml per container. Furthermore, the present invention provides the use of transformed filamentous fungal cells for the production of proteins or metabolites.

7 Claims, 2 Drawing Sheets

(56) References Cited

OTHER PUBLICATIONS

Submission in opposition proceedings made following summons to attend oral proceedings dated Oct. 9, 2013, issued in Application No. 07786832.1-1406/2032703.

Submission to attend oral proceedings pursuant to Rule 115(1) EPC, dated Jun. 12, 2013, issued in Application No. 07786832.1-1406/2032703.

DSM Reply to Communication Pursuant to Rule 79(1) EPC in the Opposition against EP 2032703 B1 dated Aug. 10, 2012 in Application No. EP07786832.1 (24 pages).

Fincham, John R.S., "Transformation in Fungi", Microbiological Reviews, Mar. 1989, vol. 53, No. 1, pp. 148-170.

Meyer et al., "Comparison of different transformation methods for Aspergillus giganteus", Current Genetics, vol. 43, No. 5, Aug. 2003, pp. 371-377, XP002447774.

Gietz et al., "Transformation of yeast by the lithium acetate/single-stranded carrier DNA/PEG method", Methods in Microbioloy, 1998, pp. 53-65, XP008082769.

HIGH THROUGHPUT TRANSFECTION OF FILAMENTOUS FUNGI

CROSS REFERENCE TO RELATED APPLICATIONS

This application is a Continuation of U.S. application Ser. No. 12,306,314 filed on Dec. 23, 2008, which is National Stage Application of PCT/EP2007/56311, filed Jun. 25, 2007, which claims priority to European Application No. 06116095.8, filed Jun. 26, 2006. Each of the foregoing is incorporated by reference in its entirety.

BACKGROUND OF THE INVENTION

1. Field of the Invention

The present invention relates to an improved method for the transfection of filamentous fungi.

2. Description of Related Art

Eukaryotic cells are preferred organisms for the production of polypeptides and secondary metabolites. In fact, filamentous fungi are widely used in large-scale industrial processes as fytase or penicillin production. To stay competitive these fermentation processes need continuous optimization. Classical strain improvement projects are widely used, but deliver only incremental improvements. New technologies as Genomics and Systems Biology in theory should be able to bring significant improvements, but until now no example has been reported for an industrial (fungal) process.

So far, examples were only reported for lab-strains and limited to few genes (Theilgaard et al, 2001, Biotechnol. Bioeng. 72:379-388; Abe et al., 2002, Mol. Genet. Genomics. 268:130-137; Askenazi et al., 2003, Nat. Biotechnol. 21:150-156). Although successful, the results are not leading to any commercial application as the productivities of such strains are several factors lower than industrial production strains. The major problem being the many leads for recombinant and targeted strain improvement coming from, for example, transcriptomics data (see Askenazi et al., 2003). With the relatively large genome size and the low genetic amenability of fungi it has not been possible to study the effect of 100+ gene modifications, let alone the combination of these. This may be the key problem causing this lack of results in industrial (fungal) applications. The average fungal genome consists of 13.000 genes, meaning that considering only the over expression of all genes leads already to 13.000 solutions. If also, deletions and kinetic alterations are considered, this number will increase further.

To decrease this number to a workable number all kinds of 'omics' technologies are applied in expensive R&D projects, collected under the name Systems Biology. However, these very huge datasets can only reduce the number of lead genes typically to several hundred. Evaluating all the combinations (say 300!) in practice, i.e. actually modifying the genes and/or expression level, still is quite laborious. Especially, considering the quite tedious transformation procedures needed to transform filamentous fungi. So, for these new technologies to deliver significant improvements in productivity of industrial fungal strains large number of transformants would have to be screened before a transformant with the properties of interest can be isolated. There is thus a need for an efficient transfection method that would enable one to quickly produce and screen many combinations and thereby increase the chance of detecting DNA sequences encoding proteins determining significant increases in process output. Present transfection systems for filamentous fungi are very laborious (see for review Fincham, 1989, Microbiol. Rev. 53:148-170). This involves protoplast formation, viscous liquid handling (i.e. polyethylene glycol solutions), one-by-one swirling of glass tubes and subsequent selective plating. On top of that the efficiency of homologous targeting was until recently very low, resulting in mostly random integrated DNA fragments, which quite often are integrated as multiple tandem repeats (see for example Casqueiro et al., 1999, J. Bacteriol. 181: 1181-1188). This uncontrolled "at random multiple integration" of an expression cassette is a potentially dangerous process, which can lead to unwanted modification of the genome of the host. It is therefore highly desirable to be able to construct a production strain by ensuring the targeting of the expression cassette to the right genomic locus with high efficiency. Both technological limitations severely hampered a rapid progress in targeted improvements of industrial fungal processes.

With the current explosion of available genome sequences and a significant improvement of homologous targeting in fungi by disturbing the non-homologous end-joining pathway (see for example Ninomiya et al., 2004, Proc. Natl. Acad. Sci. USA 101:12248-12253) it should be possible to quickly assess gene function in relation to industrial application and construct significantly improved industrial fungal strains. In addition to that also other tools are rapidly developed towards high throughput application, like the GATEWAY cloning system (Invitrogen) and genome wide GFP tagging of proteins (Toews et al., 2004, Curr. Genet. 45:383-389).

However despite those new tools being available for High Throughput functional analysis of genes, methods for High Throughput fungal transfection are lacking, hampering the application of those tools. Recently, several advances or alternatives were reported for fungal transfection methods, including:

- Efficient gene targeting and fungal transfection frequencies were obtained after *Agrobacterium tumefaciens* co-transformation (Michielse et al., 2005, Fungal Genet. Biol. 42:9-19); however this method needs co-cultivation of both species in shake flasks, and is thus not amendable for High Throughput applications.
- Genetic transformation by micro projectile bombardment (Aida V. Rodriguez-Tovar et al., 2005, J. Microbiol. Meth. 63:45-54.); this method was less efficient than *Agrobacterium*-mediated transformation and also involves one Petri-dish per experiment, and is thus not amendable for High Throughput applications.
- Electroporation seems a very fast way to transfect species and it was also established for fungi, but only for a limited set of species, like *Neurospora crassa* (Chakraborty et al., 1991, Can. J. Microbiol. 37:858-863). However, this method requires germination of conidia, resulting in a multi cellular system of which one cell may be transfected. Subsequently, this mixed cell system needs to be colony purified as only transfected cells are wanted, and therefore this method is not amendable for High Throughput applications.

So, despite many technological developments, there is no efficient and economically attractive procedure to perform high throughput transformations of filamentous fungi available, but as fungi are very important commercial species such a method is extremely desirable.

SUMMARY OF THE INVENTION

The present invention provides a method for the transfection of filamentous fungal cells, comprising the steps of:
(a) Providing a multitude of containers;
(b) Filling into each container an amount of polymer needed for the transfection;

(c) Filling the cells to be transfected as well as an aqueous solution of transfection reagent into each of the containers;
(d) Incubating the resulting mixture;
(e) Removing the transfection reagent from the incubated mixture; and
(f) Selecting the cells which have been transformed, characterized in that the total volume of the incubating mixture is less than 1 ml per container. Furthermore, the present invention provides the use of transformed filamentous fungal cells for the production of proteins or metabolites.

DETAILED DESCRIPTION OF THE INVENTION

Figure 1:
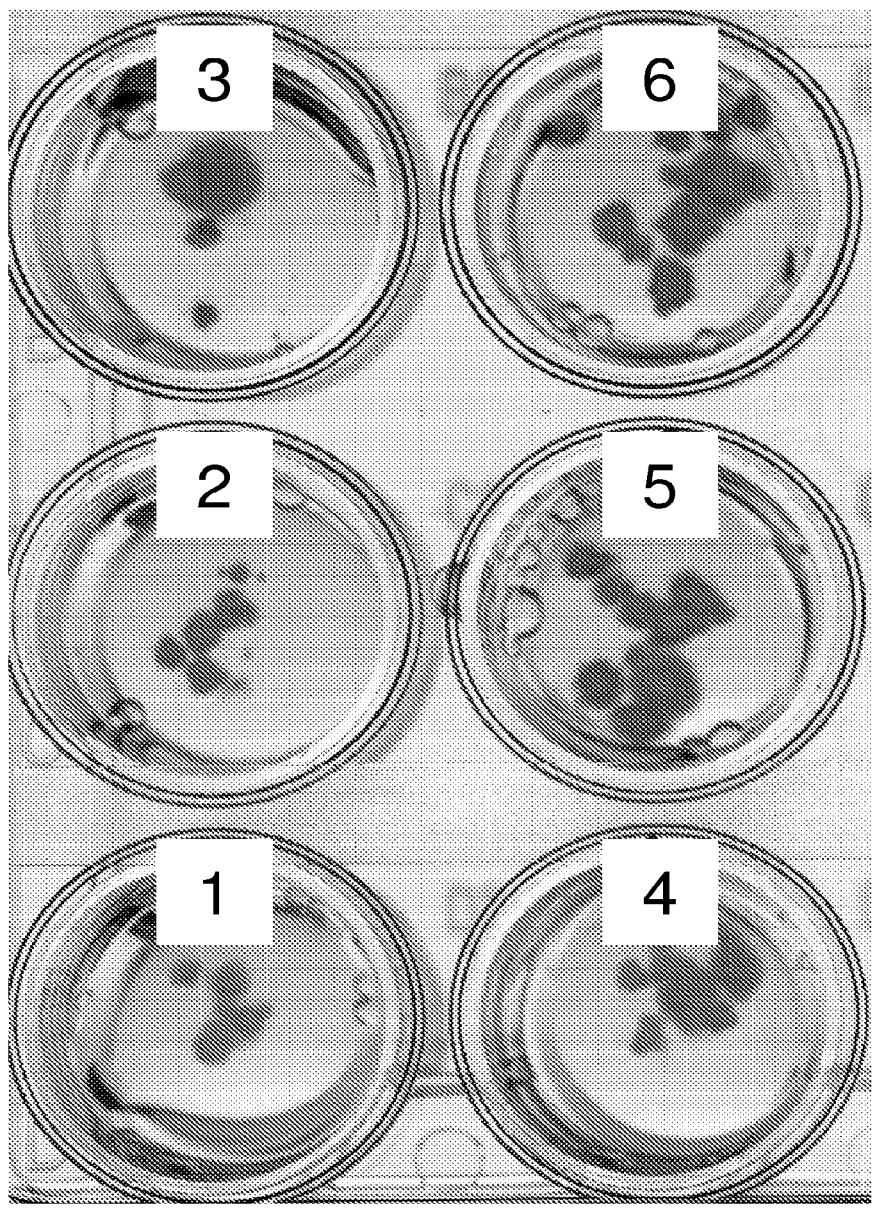
FIG. 1 shows Microtiter Plates with *Penicillium chrysogenum* transformants selected on acetamide selective agar.

It is an object of the invention to provide an improved efficient method for high throughput transfection of filamentous fungi. Surprisingly, we have found that using Micro Titer Plates (MTP's) and simple chemicals it is possible to perform hundreds to thousands of controlled and efficient fungal transfections in minimal volumes in parallel. The present invention provides a method that is able to perform thousands of controlled fungal transfections in minimal volumes in parallel and to obtain the correct transformants.

In a first aspect, a method to perform thousands of small volume fungal transformations in parallel is provided. All limitations described above can be circumvented by the method of the present invention, which will further be referred to as High Throughput Transfection (HTT). Fungal cells may be transformed by a process involving protoplast formation, protoplast transformation, and regeneration of the cell wall. Preferably, protoplasts are used, but the method is applicable to other fungal cell types. Suitable volumes in which the method is performed are those of commercially available (deepwell) MTP's, i.e. smaller than 1 ml, preferably smaller than 500 µl, more preferably smaller than 250 µl, most preferably from 1.5 µl to 250 µl, still most preferably from 10 µl to 100 µl.

The person skilled in the art will know that further fine-tuning of the present method can be obtained by alternative materials and/or formats of the Micro Titer Plate used. The method described here is not limited to 96-well format, but could well be applied to 24-well, 48-well, 384-well, 1536-well, and other Micro Titer Plate formats. Also different available shapes, forms and sizes can be applied, for example in deep-well or shallow-well format; with or without lid; with or without permeable lids; in all kinds of colors and the like. The person skilled in the art will understand that these are all state-of-the-art procedures to optimize during transfection of filamentous fungi.

Suitable procedures for preparation of protoplasts are described in EP 238,023 and Yelton et al. (1984, Proc. Natl. Acad. Sci. USA 81:1470-1474). The pre-cultivation and the actual protoplasting step can be varied to optimize the number of protoplasts and the transfection efficiency. The person skilled in the art will know that further fine tuning of the present method can be obtained by fine-tuning the present method for each species to obtain the best results, not limited to, but involving variations of inoculum size, inoculum method, pre-cultivation media, pre-cultivation times, pre-cultivation temperatures, mixing conditions, washing buffer composition, dilution ratios, buffer composition during lytic enzyme treatment, the type and/or concentration of lytic enzyme used, the time of incubation with lytic enzyme, the protoplast washing procedures and/or buffers, the concentration of protoplasts and/or DNA and/or transfection reagents during the actual transfection, the physical parameters during the transfection, the procedures following the transfection up to the obtained stably transfected cell-line. The person skilled in the art will understand that these are all state-of-the-art procedures to optimize during transfection of filamentous fungi. Protoplasts are resuspended in an osmotic stabilizing buffer. The composition of such buffers can vary depending on the species, application and needs. However, typically these buffers contain either an organic component like sucrose, citrate, mannitol or sorbitol between 0.5 and 2 M. More preferably between 0.75 and 1.5 M; most preferred is 1 M. Otherwise these buffers contain an inorganic osmotic stabilizing component like KCl, $MgSO_4$, NaCl or $MgCl_2$ in concentrations between 0.1 and 1.5 M. Preferably between 0.2 and 0.8 M; more preferably between 0.3 and 0.6 M, most preferably 0.4 M. The most preferred stabilizing buffers are STC (sorbitol, 0.8 M; $CaCl_2$, 25 mM; Tris, 25 mM; pH 8.0) or KCl-citrate (KCl, 0.3-0.6 M; citrate, 0.2% (w/v)). The protoplasts are used in a concentration between $1\times10^5$ and $1\times10^{10}$ cells/ml. Preferably, the concentration is between $1\times10^6$ and $1\times10^9$; more preferably the concentration is between $1\times10^7$ and $5\times10^8$; most preferably the concentration is $1\times10^8$ cells/ml. DNA is used in a concentration between 0.01 and 10 µg; preferably between 0.1 and 5 µg, even more preferably between 0.25 and 2 µg; most preferably between 0.5 and 1 µg. To increase the efficiency of transfection carrier DNA (as salmon sperm DNA or non-coding vector DNA) may be added to the transfection mixture.

In one embodiment of the present invention various macromolecules can be used to transform filamentous fungal cells: DNA, RNA or protein.

In yet another embodiment of the present invention the DNA sources can be: genomic DNA, cDNA, single stranded DNA, double stranded DNA, circular DNA, linear DNA, short hairpin DNA, synthetic DNA, modified DNA, labeled DNA. Also analogous forms of DNA can be applied, such as, PNA, LNA, HNA, Z-DNA, TNA. The type of vector DNA can be: cosmid, BAC, plasmid, fosmid, and the like.

In one embodiment of the present invention describes the number of different DNA molecules that can be transformed in one single experiment. These can be one or more different DNA molecules. A typical example of one DNA molecule is gene deletion construct with selection marker or a fluorescent labeled gene-of-interest (WO05040186). A typical example of two or more DNA molecules in a mixture is co-transformation with a selection marker (see for example Theilgaard et al., 2001). The transformants obtained afterwards can be analyzed with techniques like colony PCR or Southern Blotting to confirm the stable introduction of the various DNA molecules. Another example using at least two DNA molecules in a mixture is the so-called bipartite transformation (Nielsen et al., Fungal Genet. Biol. 2006 January; 43(1): 54-64). This method is using two overlapping non-functional parts of a selection marker. Upon correct homologous recombination the selection marker becomes functional. In the *Aspergillus nidulans* the method results in a 2.5-fold improvement over the standard method.

Another embodiment of the present invention is the use of selection markers active in filamentous fungi. There is a wide range of selection markers in use and all of these can be applied during the High Throughput Transfection. This can be auxotrophic markers, prototrophic markers, dominant markers, recessive markers, antibiotic resistance markers, catabolic markers, enzymatic markers, fluorescent markers, and luminescent markers. Examples of these, but not limited to, are: amdS (acetamide/fluoroacetamide), ble (phleomycin), hyg (hygromycinR), nat (nourseotricin R), pyrG (uracil/5FOA), niaD (nitrate/chlorate), sutB (sulphate/selenate), eGFP (Green Fluorescent Protein) and all the different color variants.

Another embodiment of the present invention is the use of two selection markers active in filamentous fungi. This can be applied to enhance site directed integration in filamentous fungi (Liu et al., 2001, J. Bacteriol. 183:1765-1772). The first marker is used to select in the forward mode (i.e. if active integration has occurred), while the second marker is used to select in the reverse mode (i.e. if active integration at the right locus has occurred). There is a wide range of combinations of selection markers that can be used and all of these can be applied during HTT. They can be auxotrophic markers, prototrophic markers, dominant markers, recessive markers, antibiotic resistance markers, catabolic markers, enzymatic markers, fluorescent markers, and luminescent markers. Examples of these are amdS (acetamide/fluoroacetamide), ble (phleomycin), hyg (hygromycinR), nat (nourseotricinR), pyrG (uracil/5FOA), niaD (nitrate/chlorate), sutB (sulphate/selenate), eGFP (Green Fluorescent Protein). Optimally a nuclease inhibitor is applied to prevent degradation of the nucleic acid to be transfected. Most preferably this is aurintricarboxylic acid (ATA). However, those skilled in the art understand that this can be replaced by any molecule or means with the same application. A variant of this method is described by Kang and Khang (US 2005/0181509). Here they apply a negative selection marker, i.e. the herpes simplex virus thymidine kinase (HSVtk) gene, as the second selection marker. If the selection procedure would work correctly, polynucleotides that integrate at random in the genome would kill the cells as the HSVtk gene would convert the 5-fluoro-2'-deoxyurine in the agar plates to a toxic compound.

Another embodiment of the present invention is the use of fluorescently labeled polymers (i.e. DNA, RNA or protein) to be introduced in the host cell via HTT. An example of such a method is described in WO05040186. The advantages of this method are that marker-free transformants can be obtained and multiple-colors can be used.

One embodiment of the present invention describes the addition of nuclease inhibitors, to prevent host-specific degradation of the incoming nuclei acids. The most widely used Is Aurintricarboxylic acid (ATA). Alternatively, general or specific protease inhibitors, like PMSF or specific antibodies, can be used to prevent the host-specific degradation of the incoming proteins.

One particular embodiment of the present invention describes the transfection reagent. The scope of the invention is not limited to the examples given in which Polyethylene Glycol (PEG) is used, but can be extended to any suitable transfection reagent available. Suitable transfection reagents are FUGENE® HD (from Roche), Lipofectamine™ or OLIGOFECTAMINE™ (from Invitrogen), TRANSPASS™ D1 (from New England Biolabs), LYPOVEC™ or LIPOGEN™ (from Invivogen). However, for filamentous fungi PEG is the most preferred transfection reagent. PEG is available at different molecular weights and can be used at different concentrations. Preferably PEG 4000 is used between 10% and 60%, more preferably between 20% and 50%, most preferably at 30%.

Another embodiment of the present invention describes the handling of the Micro Titer Plates and pipetting of solutions. This can be manually, but preferably this is performed semi-automated and most preferably this is performed fully automated.

The method described can be applied to the following filamentous fungal species, but is not limited to: *Aspergillus niger* CBS 513.88, *Aspergillus nidulans*, *Aspergillus oryzae* ATCC 20423, IFO 4177, ATCC 1011, ATCC 9576, ATCC14488-14491, ATCC 11601, ATCC12892, *Penicillium chrysogenum* ATCC 28089, *Penicillium chrysogenum* CBS 455.95, *Penicillium citrinum* ATCC 38065, *Penicillium chrysogenum* P2, *Acremonium chrysogenum* ATCC 36225 or ATCC 48272, *Trichoderma reesei* ATCC 26921 or ATCC 56765 or ATCC 26921, *Aspergillus sojae* ATCC11906, *Chrysosporium lucknowense* ATCC44006, *Penicillium brevicompactum* ATCC16025, ATCC9056 or FERMP-5693, *Glarea lozoyensis* ATCC74030, ATCC20957, *Aspergillus terreus* ATCC20542 and derivatives thereof.

In one embodiment, specific mutants of the fungal species are used which are extremely suitable for the HTT method. These can be obtained via classical screening methods or via recombinant approaches. Examples of such mutants are strains that protoplast very well; strains that produce mainly or, more preferably, only protoplasts with a single nucleus; strains that regenerate very well in MTP's; strains that regenerate faster and strains that take up (DNA) molecules very efficiently.

In another embodiment of the present invention specific mutants of the fungal species are used which are modified in their DNA repair system in such a way that they are either incapable of integrating DNA, extremely efficient in homologous recombination, extremely efficient in integrating multiple copies of the donor DNA, or, alternatively, extremely efficient in random integration. Examples of such mutants are: ku70, ku80, mre11, rad51, rad52, rad54. The efficiency of targeted integration of a nucleic acid construct into the genome of the host cell by homologous recombination, i.e. integration in a predetermined target locus, is preferably increased by augmented homologous recombination abilities of the host cell. Such phenotype of the cell preferably involves a deficient hdfA or hdfB gene as described in WO 05/95624. WO 05/95624 discloses a preferred method to obtain a filamentous fungal cell comprising increased efficiency of targeted integration.

Another embodiment of the present invention is the use cell sorting systems to enhance the throughput and output of the High Throughput Transfection method. Cells can be pre-sorted before the actual transfection. This can be done on nuclear content, cell size, cell integrity, cell viability, cell composition, specific staining methods, and the like. Also, post-transfection sorting can be done. This can be done on nuclear content, cell size, cell integrity, cell composition, cell viability, specific staining methods, and the like. A more preferred post-transfection sorting is based on the fluorescent labeling of DNA molecules and the subsequent transfection as disclosed by WO05040186. Preferred apparatus to be used are Fluorescent Cell Sorters.

Another embodiment of the present invention describes the use of different washing buffers after the actual transformation experiment to remove the transfection reagents, so before plating the cells. This can be any type of buffer, although an osmotic stabilizer must be present. Preferred buffers are: STC, KCl-citrate or KCl (0.3-0.6 M).

Another embodiment of the present invention describes the use of so-called supportives to the wells of the MTP's. For example this can be filters on top of the agar. These will prevent the growth of the fungus into the agar, which will enable easy handling later on. Also, it can work as a direct supportive for the more efficient regeneration of protoplasts and thus leads to more transformants.

Another embodiment of the present invention is the induction of sporulation after transfection. As most fungal species are multi-nucleate during the hyphal or vegetative life-stage, protoplasts contain also mostly more than one nucleus and sporulation will lead to single nucleus spores. Sporulation can be induced via different methods. The most widely used is the transfer of the transformants from the regeneration plate to an agar medium inducing sporulation. Preferably, the regeneration medium is developed in such a way that also sporulation is induced. Preferably, this is obtained via the use of rich medium or mineral medium with salts (i.e. KCl, $MgSO_4$) as the osmotic stabilizer. If sporulation is not complete and a mixture of cells with different numbers of nuclei are obtained, one could use a DNA staining method and a Flow cytometer with cell sorting to isolate the cells with a single nucleus. These can be isolated in such a way that pure and stable cell-lines are obtained. Ideally this is all done in the same format in Micro Titer Plates.

Another embodiment of the present invention is the screening of the thus obtained transformants for altered production levels, morphology, growth rates, altered side product levels, altered color, resistance, and the like.

A second aspect of the present invention is to use the selected transformants to produce proteins or metabolites.

EXAMPLES

Example 1

Transformation of *Penicillium chrysogenum* Using Microtiter Plate

*Penicillium chrysogenum* protoplasts are prepared as disclosed WO199932617 and WO199846772. They were either stored on ice (during the day) or at −80° C. To each well in the Microtiter Plate 4 µl of DNA solution (0.25 µg/µl pHELYA1, see WO 04/106347) with the right concentration is added. pHELYA1 is an integrative vector with the amdS selection marker gene, encoding acetamidase, enabling transformants to grow on media with acetamide as the sole nitrogen source. Next a nuclease inhibitor (Aurintricarboxylic acid, ATA, 20 mM), the protoplasts and a polymer (Polyethylene Glycol, PEG, 200 g/l in STC; sorbitol, 0.8 M; $CaCl_2$, 25 mM; Tris, 25 mM; pH 8.0) are added, according to Table 1.

TABLE 1

Components for *Penicillium chrysogenum* HTT in Microtiter Plates

| Component | Deepwell 96-wells MTP (in µl) |
|---|---|
| DNA | 4 |
| ATA | 2.5 |
| Protoplasts (1 × 10$^8$/ml) | 25 |
| PEG 20% | 12.5 |

Figure 2:
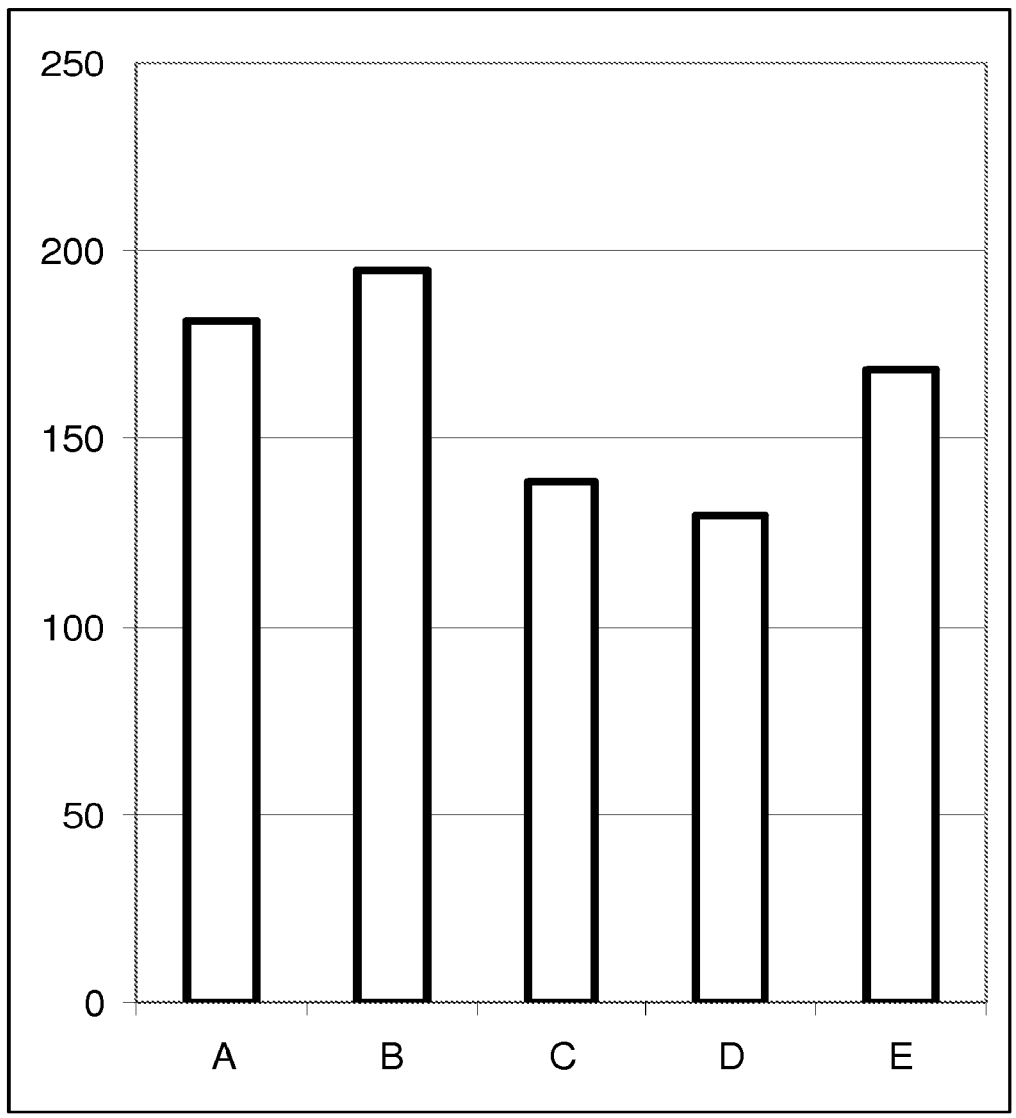
FIG. 2 shows the transformants obtained with *Penicillium chrysogenum* by the HTT method. Legend: Y-axis=number of transformants per 50 µl of protoplasts (or 2 µg of DNA); X-axis=different protocols (A=standard glass tube protocol with manual pipetting and swirling; B=MTP with semi-automated pipetting and swirling; C=MTP with semi-automated pipetting and mixing; D=MTP with hand pipetting and swirling; E=MTP with hand pipetting and mixing).

The addition is done manually (pipetting) and automated (for example with a Multidrop from Thermo Electron Corporation). The mixture is mixed carefully, either via swirling or via pipetting up-and-down. Subsequently, the mixtures are incubated on ice for 30 minutes and 190 µl/well of 30% PEG is added. No mixing is required at this step. The whole Micro Titer Plate is incubated for 15 minutes at 25° C. After which 700 µl/well STC is added. No mixing required. The Micro Titer plate is centrifuged for 5 min at 1500 rpm. The supernatant is discarded and the cell pellets are resuspended in 100 µl/well STC. The cell-suspensions are transferred at different dilutions to selective acetamide agar (see WO199932617 and WO199846772) well Micro Titer Plates and incubated for 5 to 7 days at 25° C. As indicated in FIG. 1, these agar well Micro Titer Plates are well suited for this purpose, as individual transformants can be obtained. As a control the standard glass tube transfection was performed. All transfection procedures typically yielded around 200 transformants per 50 µl of protoplast solution, which corresponds to approximately 100 transformants per µg DNA (see FIG. 2). This result demonstrates that the High Throughput Transfection is a very efficient transfection method.

Example 2

Transfection of *Aspergillus niger* in Microtiter Plate

*Aspergillus niger* protoplasts for MTP transfection are prepared according to the protocol for transformation in WO199932617 and WO199846772, resulting in a protoplasts suspension of 1×10$^8$ protoplasts/ml in STC. These protoplasts are transformed using either undigested or linearized donor DNA. Transfection and subsequent selection of transformants is performed as in Table 2, listing the individual steps of the *Aspergillus niger* MTP transfection protocol. Transformants are plated in MTP's containing SRM (see WO199932617 and WO0199846772) supplemented with 150 µg/ml phleomycin and grown for 6-7 days at 30° C. The resulting transformants are transferred from the 1$^{st}$ selection plate to 20$^{nd}$ selection plates (PDA supplemented with 150 µg/ml phleomycin; see WO199932617 and WO199846772) and subsequently grown for 5 to 7 days at 30° C. Copies of the 2$^{nd}$ selection plates are made on PDA in MTP (preferably with phleomycin) using a 96-pin gridder. Using the procedure described above various DNA concentrations were used to test the efficiency of the HTT procedure. For this purpose, undigested DNA of an integrative plasmid (pGBFIN; WO199932617) was used to transform *Aspergillus niger* protoplasts. The optimal DNA concentration for MTP transfection was in the range of 0.5-1.0 µg/µl DNA, yielding between 50 and 100 transformants per well.

TABLE 2

Detailed protocol for *Aspergillus niger* HTT in Micro Titer Plates

| Step | Volume/Remarks |
|---|---|
| First Selection | |
| MTP plate | 400 µl in Wide well MTP (96) |
| + DNA | 5 µl (manual) |
| + Protoplasts/ATA/20% PEG$^1$ | 35 µl |
| 10 min. Room Temperature | |
| + 30% PEG | 90 µl |
| 20 min. Room Temperature | |
| + Sorbitol 1.2M | 250 µl |
| Total volume | 380 µl |
| MTP centrifuge | Spin 5 min., 1500 rpm |
| Aspirate remaining liquid | |
| + Sorbitol 1.2M | 20 µl |

TABLE 2-continued

Detailed protocol for *Aspergillus niger* HTT in Micro Titer Plates

| Step | Volume/Remarks |
|---|---|
| Resuspend and transfer to MTP containing SRM agar with phleomycin[2] Grow 5-7 days at 30° C. | 20 µl |
| Second Selection | |
| Transfer spores with 10% glycerol/ 0.05% Triton-X100 on PDA agar with phleomycin[2] Grow 6-7 days at 30° C. | 100 µl 2 × 30 µl |

[1]Mix (for 8 MTP's); 2 ml ATA, 10 ml 20% PEG, 10 ml STC, 10 ml 1 × 10$^8$/ml protoplasts
[2]150 µg/ml phleomycin Example 3

Co-Transfection of *Penicillium chrysogenum* in Microtiter Plate

*Penicillium chrysogenum* protoplasts were prepared as disclosed in WO199932617 and WO199846772 and stored on ice or at −80° C. To each well in the Micro Titer Plate 4 µl of DNA solution (either 0.25 µg/µl pHELYA1; or a mixture of 0.25 µg/µl pHELYA1 and 0.25 µg/µl pISEWA, see WO 04/106347) with the right concentration was added. The pHELYA1 vector and use is as described in Example 1. pISEWA is an integrative vector containing the *Streptomyces clavuligerus* gene cefE, encoding expandase, an enzyme that can expand the five-membered penicillin ring into the six-membered cephalosporin ring. Selection on acetamide was used to select transformants, followed by a cephalosporin specific bioassay to determine the co-transformation efficiency. The procedure from Example 1 was followed. Thus, to the DNA the nuclease inhibitor ATA, the protoplasts and the 20% PEG were added, according to Table 1. A few variables were changed, including either 30% or 60% PEG in the second step and mixing or no mixing in the second step (Table 3). As a control a standard transfection was performed in glass tubes (see WO199932617 and WO199846772). These were performed with 200 µl protoplasts and the added volumes of all other solutions were increased likewise (thus 8×). As can be seen from Table 3 all transfections with DNA gave a sufficient number of transformants. Approximately 40 colonies of each transfection were processed for bioassay by transfer to an agar-solidified version of the penicillin production medium as disclosed by US20020039758, without phenoxyacetic acid. The cells were grown for 4 days and then overlayed with a top-agar version of 2xYT (Sambrook et al., 1989, Molecular cloning: a laboratory manual, 2$^{nd}$ Ed., Cold Spring Harbor Laboratory Press, Cold Spring Harbor, N.Y.; with 0.8% agar), to which as antibiotic indicator organism *Escherichia coli* ESS was added. To degrade the penicillins made by all *Penicillium* strains penicillinase (Penase from DIFCO) was added to the top-agar. The plates were incubated overnight at 37° C. and co-transformants were scored by the presence of a halo around the colony, indicating that bacterial growth was inhibited by the production of cephalosporins. If co-transformation was successful, this took place 10 to 20% of the transformants. Also there was no significant difference observed in the co-transformation frequency obtained via the standard glass-tube protocol or this High Throughput Transfection method using Micro Titer Plates.

TABLE 3

Co-transformation results *Penicillium chrysogenum* HTT in Microtiter Plates

| Trans-fection | DNA | PEG (%) | mix | CFU (#/50 µl protoplasts) | Bio-Assay positive | Co-trans-formants (%) |
|---|---|---|---|---|---|---|
| MTP | — | 30 | Y | 0 | 0 | 0 |
| | — | 60 | Y | 0 | 0 | 0 |
| | pHELYA1 | 30 | Y | 29 | 0 | 0 |
| | | 30 | N | 54 | 0 | 0 |
| | pHELYA1 | 30 | Y | 11 | 0 | 0 |
| | | 30 | N | 18 | 0 | 0 |
| | pHELYA1 | 60 | Y | 98 | 0 | 0 |
| | | 60 | N | 80 | 0 | 0 |
| | pHELYA1 + pISEWA | 30 | Y | >300 | 0 | 0 |
| | | 60 | Y | >300 | 0 | 0 |
| | | 30 | N | 418 | 0 | 0 |
| | | 30 | N | 344 | 4/40 | 10 |
| | | 60 | N | 420 | 5/40 | 12.5 |
| | pHELYA1 + pISEWA | 30 | Y | 101 | 0 | 0 |
| | | 60 | Y | 212 | 0 | 0 |
| | | 30 | N | 132 | 0 | 0 |
| | | 30 | N | 138 | 6/40 | 15 |
| | | 60 | N | 212 | 0 | 0 |
| Glass Tube | — | 60 | Y | 0 | 0 | 0 |
| | pHELYA1 | 60 | Y | 572 | 0 | 0 |
| | pHELYA1 + pISEWA | 60 | Y | >>300 | 7/40 | 17.5 |
| | pHELYA1 | 60 | Y | 492 | 0 | 0 |
| | pHELYA1 + pISEWA | 60 | Y | >>300 | 6/36 | 16.7 |

Example 4

Transfection of *Penicillium chrysogenum* in Microtiter Plate

*Penicillium chrysogenum* protoplasts are prepared as disclosed in WO199932617 and WO199846772. They were either stored on ice (during the day) or at −80° C. at 1×10$^8$ protoplasts/ml in STC. Prior to the transfection 4 µl of DNA solution (0.5 µg of a plasmid with the amdS gene, for example pHELYA1 as described in WO 04/106347) was added to wide-well MTP's (Nunc U96 MicroWell™ Plates—Polypropylene (cat. No. 267334)). Thawed protoplasts were added together with ATA and PEG20% to the DNA and incubated in a 4° C. cold room. The details of the transfection and subsequent selection of transformants are depicted in Table 4.

TABLE 4

Detailed protocol for *Penicillium chrysogenum* HTT in Wide Well Micro Titer Plates

| Step | Volume/Remarks |
|---|---|
| First Selection | |
| MTP plate | Nunc U96 MicroWell ™ Plates - Polypropylene (cat. No. 267334) |
| + DNA | 4 µl |
| + Protoplasts/ATA/20% PEG4000[1] | 40 µl |
| 30 min. 4° C. cold room | Put on a cold surface |
| + 30% PEG4000 | 90 µl |
| 15 min. 25° C. | |
| + KCl-Citrate | 250 µl |
| Spin down in MTP centrifuge Pipette off liquid | 5 min., 1500 rpm |
| + KCl-Citrate | 100 µl (when using 24-well MTP) 20 µl (when using 96-well MTP) |
| Resuspend and transfer to MTP | 100 µl (when using 24-well MTP) |

TABLE 4-continued

Detailed protocol for *Penicillium chrysogenum* HTT in Wide Well Micro Titer Plates

| Step | Volume/Remarks |
| --- | --- |
| containing Mineral Medium agar with acetamide and 0.3M KCl Grow for 7 days at 25° C. | 20 μl (when using 96-well MTP) |
| Second Selection | |
| Resuspend spores with H20 (optionally with 0.001-0.05% Triton-X100) | 1000 μl |
| Transfer to Mineral Medium agar with acetamide Grow 5-7 days at 25° C. | 100 μl |

[1]Mix (for 1 MTP): 2.5 ml protoplasts (1 × 10$^8$/ml), 0.25 ml ATA, 1.25 ml 20% PEG4000

Transformants are plated in standard 24-well MTP's containing Mineral Medium (as described in WO04106347 without phenylacetic acid, but with agar (15 g/l), acetamide (0.1%) and KCl (0.3 M)). Typically 20-100 transformants were obtained after 7 days at 25° C. After sporulation the transformants were transferred from the regeneration plate to a 2$^{nd}$ amdS selection plates (the same medium as above, but without the KCl). This is done automatically by adding 1 ml of H$_2$O, to make a spore suspension. Typically, 100 μl is sufficient to get sufficient growth on the 2$^{nd}$ amdS selection plate. From this one can make a Master Cell Bank for further tests and applications

What is claimed is:

1. A high throughput method for transfection of filamentous fungal cells, comprising:
   (a) providing a multitude of containers;
   (b) filling into each container an amount of polymer needed for the transfection;
   (c) filling the cells to be transfected as well as an aqueous solution of transfection reagent into each of the containers;
   (d) incubating the resulting mixture;
   (e) optionally removing the transfection reagent from the incubated mixture; and
   (f) selecting the cells which have been transformed, characterized in that the total volume of the incubating mixture is less than 1 ml per container, wherein said polymer of step (b) is DNA or RNA, and wherein said transfection reagent of step (c) is polyethylene glycol 4000, and wherein the aqueous solution of step (c) contains not more than 30% of polyethylene glycol.

2. The method according to claim 1, wherein said volume is less than 250 μl.

3. The method according to claim 1, wherein the cells of step (c) are protoplasts.

4. The method according to claim 1, wherein the incubation of step (d) is interrupted at least once, whereupon an additional amount of an aqueous solution of polyethylene glycol is filled into each of the containers.

5. The method according to claim 4, wherein the additional amount of aqueous solution contains not more than 30% polyethylene glycol.

6. The method according to claim 1, wherein step (f) comprises growing the cells in a container containing a volume of growth medium of less than about 2000 μl per container.

7. A method of producing proteins or metabolites
   (a) providing a multitude of containers;
   (b) filling into each container an amount of polymer needed for the transfection;
   (c) adding filamentous fungal cells to be transfected and an aqueous solution of transfection reagent to each container, wherein the total volume of said cells and said reagent is less than 1 ml per container;
   (d) incubating the resulting mixture;
   (e) optionally removing the aqueous solution of transfection reagent from the incubated mixture;
   (f) selecting the cells which have been transformed, and
   (g) culturing said transformed cells, thereby producing said proteins or metabolites;
wherein said polymer of step (b) is DNA or RNA, and wherein said transfection reagent of steps (c) and (e) is polyethylene glycol 4000, and wherein the aqueous solution of step (c) contains not more than 30% of polyethylene glycol.

* * * * *